United States Patent
Nakano

(10) Patent No.: US 9,089,558 B2
(45) Date of Patent: Jul. 28, 2015

(54) PACKAGED PRODUCT OF SOLID PREPARATION CONTAINING 5-HYDROXY-1H-IMIDAZOLE-4-CARBOXAMIDE OR SALT THEREOF, OR HYDRATE THEREOF

(71) Applicant: FUJIFILM Corporation, Tokyo (JP)

(72) Inventor: Shumma Nakano, Toyama (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 14/528,798

(22) Filed: Oct. 30, 2014

(65) Prior Publication Data
US 2015/0051408 A1 Feb. 19, 2015

Related U.S. Application Data

(63) Continuation of application No. PCT/JP2014/050592, filed on Jan. 15, 2014.

(30) Foreign Application Priority Data

Jan. 15, 2013 (JP) ................. 2013-004996

(51) Int. Cl.
| | | |
|---|---|---|
| *C07D 233/90* | (2006.01) | |
| *A61K 31/4164* | (2006.01) | |
| *A61K 9/16* | (2006.01) | |
| *A61K 9/20* | (2006.01) | |
| *A61K 9/28* | (2006.01) | |
| *A61J 1/03* | (2006.01) | |
| *C07D 233/70* | (2006.01) | |

(52) U.S. Cl.
CPC ........... *A61K 31/4164* (2013.01); *A61K 9/1652* (2013.01); *A61K 9/2054* (2013.01); *A61K 9/282* (2013.01); *A61J 1/03* (2013.01); *C07D 233/70* (2013.01); *C07D 233/90* (2013.01)

(58) Field of Classification Search
CPC ........... A61K 31/4164; A61K 31/4166; C07D 233/90
USPC .................................................. 514/400, 386
See application file for complete search history.

(56) References Cited

U.S. PATENT DOCUMENTS

| 4,181,731 A | * | 1/1980 | Yoshida et al. ............... 514/386 |
| 4,582,845 A | * | 4/1986 | Yamahira et al. ............. 514/398 |
| 2010/0210855 A1 | * | 8/2010 | Nobuo et al. ............. 548/323.1 |

FOREIGN PATENT DOCUMENTS

| EP | 159777 A1 * | 10/1985 |
| JP | 53-32124 A | 3/1978 |
| JP | 57-80328 A | 5/1982 |
| JP | 59-36624 A | 2/1984 |

OTHER PUBLICATIONS

International Search Report, mailed Apr. 22, 2014, issued in PCT/JP2014/050592.
Kenji Fukumuro, "Device for improving compliance 2", Clinician, No. 405, pp. 1019-1022, 1991.
Written Opinion of the International Searching Authority, mailed Apr. 22, 2014, issued in PCT/JP2014/050592.

* cited by examiner

*Primary Examiner* — Matthew Coughlin
(74) *Attorney, Agent, or Firm* — Birch, Stewart, Kolasch & Birch, LLP

(57) ABSTRACT

The present invention provides a packaged product of a solid preparation containing 5-hydroxy-1H-imidazole-4-carboxamide or a salt thereof, or a hydrate thereof, which comprises the solid preparation and an environment-controlling agent packaged together. The packaged product of present invention is useful as a packaged product of a solid preparation containing 5-hydroxy-1H-imidazole-4-carboxamide or a salt thereof, or a hydrate thereof, with which discoloration of the solid preparation is suppressed, and superior storage stability of the solid preparation is obtained.

13 Claims, No Drawings

PACKAGED PRODUCT OF SOLID PREPARATION CONTAINING 5-HYDROXY-1H-IMIDAZOLE-4-CARBOXAMIDE OR SALT THEREOF, OR HYDRATE THEREOF

CROSS REFERENCE TO RELATED APPLICATIONS

This application is a Continuation of International Application No. PCT/JP 2014/050592 filed on Jan. 15, 2014, which claims the benefit of Japanese Patent Application No. 2013-004996 filed on Jan. 15, 2013. The entire contents of all of the above applications are hereby incorporated by reference.

TECHNICAL FIELD

The present invention relates to a packaged product for stably storing a solid preparation containing 5-hydroxy-1H-imidazole-4-carboxamide or a salt thereof, or a hydrate thereof.

BACKGROUND ART

Since 5-hydroxy-1H-imidazole-4-carboxamide (henceforth also referred to as Compound A) or a salt thereof, or a hydrate thereof has a potent carcinostatic action, it is a medically useful compound as an anticancer agent (Patent document 1). In particular, it is an anticancer agent that exhibits a potent efficacy against solid carcinomas, against which chemotherapy has conventionally been considered difficult, and is a highly safe anticancer agent that shows less side reactions, and thus it is a compound of which clinical applications are expected in a wide range of dosage forms such as oral agent, injection, ointment, and suppository. The dosage form generally most preferred by patients is tablet (Non-patent document 1).

Compound A has a characteristic that it is easily discolored by oxygen, heat, light, or the like, and when it is made into, for example, an oral preparation, it is affected by interactions of coexisting excipient, and thus tends to show further notable discoloration (Patent document 2).

So far, as a means for preventing such discoloration concerning pharmaceutical preparation design, a method of using a sulfur compound is known (Patent document 3). Further, as a means for preventing discoloration of Compound A, there is known a method of coexisting a solid preparation of Compound A and a commonly used self-activating type deoxidant or deoxidating and carbon dioxide gas-generating agent is known (Patent document 2).

PRIOR ART REFERENCES

Patent Documents

Patent document 1: Japanese Patent Unexamined Publication (Kokai) No. 53-32124
Patent document 2: Japanese Patent Unexamined Publication (Kokai) No. 59-36624
Patent document 3: Japanese Patent Unexamined Publication (Kokai) No. 57-80328

Non-patent Document

Non-patent document 1: Kenji Fukumuro, "Device for improving compliance 2", CLINICIAN, No. 405, p.1020, 1991

DISCLOSURE OF THE INVENTION

Object to be Achieved by the Invention

Sulfur compounds used for preventing discoloration exhibit potent effect for preventing discoloration of Compound A, but preparations utilizing a sulfur compound give odor peculiar to sulfur compounds when such preparation are taken, and such sulfur compounds are not necessarily satisfactory means for use in solid preparations.

Further, the method of coexisting a solid preparation of Compound A and a commonly used self-activating type deoxidant or deoxidating and carbon dioxide gas-generating agent cannot provide discoloration preventive effect required for practical use.

Therefore, there is desired a stable packaged product of a solid preparation containing Compound A or a salt thereof, or a hydrate thereof with which the discoloration during storage is suppressed to a level acceptable for practical use.

Means for Achieving the Object

Under such circumstances, the inventor of the present invention paid attention to moisture, of which influence on the stability has not conventionally been taken into consideration, and surprisingly found that moisture influenced on the discoloration at a degree equivalent to or higher than that of oxygen. Furthermore, the inventor of the present invention also found that, among various deoxidants, a deoxidant based on a specific mechanism had a discoloration preventing effect. The inventor of the present invention further conducted various researches, and as a result, accomplished a stable packaged product comprising Compound A or a salt thereof, or a hydrate thereof, with which the discoloration during storage was suppressed to a level acceptable for practical use.

The present invention thus provides a packaged product of a solid preparation containing Compound A or a salt thereof, or a hydrate thereof, which comprises the solid preparation and an environment-controlling agent packaged together.

The present invention also provides a method for stabilizing a solid preparation containing Compound A or a salt thereof, or a hydrate thereof, which comprises packaging the solid preparation and an environment-controlling agent together.

[1] A packaged product of a solid preparation containing Compound A or a salt thereof, or a hydrate thereof which comprises the solid preparation and an environment-controlling agent packaged together.
[2] The packaged product of the solid preparation according to [1], wherein the environment-controlling agent is a desiccant, a deoxidant that exhibits a deoxidation function in a dry atmosphere, or a deoxidant having both a deoxidation function and a desiccation function.
[3] The packaged product of the solid preparation according to [1], wherein the environment-controlling agent is a desiccant.
[4] The packaged product according to [2] or [3], wherein the desiccant is silica gel.
[5] The packaged product of the solid preparation according to [3] or [4], wherein the deoxidant that exhibits a deoxidation function in a dry atmosphere is further packaged together.
[6] The packaged product of the solid preparation according to [2] or [5], wherein the deoxidant that exhibits a deoxidation function in a dry atmosphere is a deoxidant using oxidation of carbon-carbon unsaturated bond.

[7] The packaged product of the solid preparation according to [3] or [4], wherein a self-activating type deoxidant is further packaged together.

[8] A method for stabilizing a solid preparation containing Compound A or a salt thereof, or a hydrate thereof, which comprises packaging the solid preparation together with an environment-controlling agent.

[9] The method for stabilizing the solid preparation according to [8], wherein the environment-controlling agent is a desiccant, a deoxidant that exhibits a deoxidation function in a dry atmosphere, or a deoxidant having both a deoxidation function and a desiccation function.

[10] The method for stabilizing the solid preparation according to [8], wherein the environment-controlling agent is a desiccant.

[11] The method for stabilizing the solid preparation according to [9] or [10], wherein the desiccant is silica gel.

[12] The method for stabilizing the solid preparation according to [10] or [11], wherein a deoxidant that exhibits a deoxidation function in a dry atmosphere is further packaged together.

[13] The method for stabilizing the solid preparation according to [9] or [12], wherein the deoxidant that exhibits a deoxidation function in a dry atmosphere is a deoxidant using oxidation of carbon-carbon unsaturated bond.

[14] The method for stabilizing the solid preparation according to [10] or [11], wherein a self-activating type deoxidant is further packaged together.

Effect of the Invention

According to the present invention, it becomes possible to suppress discoloration of a solid preparation containing Compound A or a salt thereof, or a hydrate thereof during storage to a level acceptable for practical use, and thus there can be provided such a packaged product that shows superior storage stability.

MODES FOR CARRYING OUT THE INVENTION

Hereafter, the present invention will be explained in detail.

The symbol "%" used for the present invention means percentage by mass, unless especially indicated. The numerical value ranges shown with "to" in the present invention means ranges including the numerical values indicated before and after "to" as the minimum and maximum values, respectively. In the present invention, when two or more kinds of substances corresponding one component of a composition are present in the composition, the amount of the component means the total amount of the two or more kinds of substances present in the composition, unless especially indicated.

When the expression "Compound A or a salt thereof, or a hydrate thereof" is used in this invention concerning Compound A (also concerning the indication of "5-hydroxy-1H-imidazole-4-carboxamide"), it is intended to indicate at least one selected from the group consisting of Compound A, a salt of Compound A, a hydrate of Compound A, and a hydrate of a salt of Compound A, unless especially indicated, and the expression "containing Compound A or a salt thereof, or a hydrate thereof" means to contain at least one selected from the group consisting of Compound A, a salt of Compound A, a hydrate of Compound A, and a hydrate of a salt of Compound A, unless especially indicated.

The term "discoloration" used in this specification means that apparent change of white color into a color other than white color, or apparent change of a color other than white color into another color other than white color.

The term "level acceptable for practical use" used in this specification means that, for example, when color difference ($\Delta E^*$) is measured for surface of a solid preparation before and after storage for three months under the conditions of 40° C. and a relative humidity of 75% by using a color difference meter, the color difference ($\Delta E^*$) is not larger than 3. Further, it also means that, for example, when color difference ($\Delta E^*$) is measured for surface of a solid preparation before and after storage for four weeks under the condition of 60° C. by using a color difference meter, the color difference ($\Delta E^*$) is not larger than 3.

Compound A or a salt thereof, or a hydrate thereof used for the present invention can be produced by, for example, the method described in Preparation Example 1 mentioned later.

The term "package" used in the present invention means to enclose an object (solid preparation or solid preparation enclosed in a permeable packaging container) in a light, moisture, or oxygen nonpermeable or hardly permeable packaging container, preferably a light, moisture, and oxygen nonpermeable or hardly permeable packaging container.

The "packaged product" referred to in the present invention means one consisting of at least a solid preparation containing 5-hydroxy-1H-imidazole-4-carboxamide or a salt thereof, or a hydrate thereof and a packaging container enclosing the solid preparation. The "packaged product" can also be expressed as "packaged article", "packaged solid preparation", "solid preparation enclosed in a packaging container", or the like.

The "environment-controlling agent" referred to in the present invention means a desiccant, a deoxidant that exhibits a deoxidation function in a dry atmosphere, or a deoxidant having both a deoxidation function and a desiccation function.

The "desiccant" used in the present invention is not particularly limited, so long as it is a desiccant used for medical use, and examples include, for example, silica gel, calcium chloride, slaked lime, dried plastics (super absorbent polymer), silica-alumina type clay (allophane), zeolite, "moisture-absorbing film package formed from a film having a moisture-absorbing property consisting of a resin incorporated with synthetic zeolite" such as MoistCatch (Kyodo Printing), and so forth. Preferred examples include silica gel and zeolite, and more preferred examples include silica gel.

The "deoxidant that exhibits a deoxidation function in a dry atmosphere" used in the present invention means a deoxidant designed so as to exhibit a deoxidation function in a dry atmosphere without requiring any moisture donor. Examples include, for example, a "deoxidant using oxidation of carbon-carbon unsaturated bond", such as PharmaKeep KH (Mitsubishi Gas Chemical), "deoxidant comprising an oxygen-absorbing composition", which comprises a composition containing a liquid hydrocarbon oligomer having an unsaturated group as a main component and an oxygen absorption promoting agent carried on a carrier, "deoxidant comprising a metal as a main component", which is prepared by disposing a transition metal on a carrier, and activating the metal, "deoxidant comprising activated magnesium as a main component", which is obtained by disposing a magnesium compound on a carrier, and then reducing the magnesium compound, "oxygen-absorbing film not requiring moisture for oxygen absorption and containing a cerium oxide type deoxidant at high density" such as OxyCatch (Kyodo Printing), and so forth, and preferred examples include a "deoxidant using oxidation of carbon-carbon unsaturated bond".

The "deoxidant having both a deoxidation function and a desiccation function" referred to in the present invention means a deoxidant designed to comprise a deoxidant and a desiccant combined beforehand, and examples include, for example, a "deoxidant comprising a deoxidant using oxidation of carbon-carbon unsaturated bond and silica gel combined beforehand", such as PharmaKeep KD (Mitsubishi Gas Chemical).

The "self-activating type deoxidant" referred to in the present invention means a deoxidant designed so that moisture required for deoxidation is supplied from a moisture donor made to exist in the deoxidant, and examples include, for example, Ageless ZP (Mitsubishi Gas Chemical), and so forth.

The deoxidant that exhibits a deoxidation function in a dry atmosphere, and the self-activating type deoxidant are preferably packaged together with a desiccant.

Form of the solid preparation containing Compound A or a salt thereof, or a hydrate thereof is not particularly limited, and examples include, for example, powder, subtilized granule, granule, dry syrup, capsule, and tablet. Preferred examples include granule (preparation granulated into particles for oral administration, including subtilized granule unless especially indicated) and tablet, and more preferred examples include tablet.

Examples of the tablet include uncoated tablet, sugar-coated tablet, film-coated tablet, and so forth, and preferred examples include film-coated tablet.

Any type of the solid preparation can be preferably combined with an arbitrary environment-controlling agent selected from those mentioned above. Particularly preferred examples of the combination include a combination of a tablet or granules, and a desiccant, a deoxidant that exhibits a deoxidation function in a dry atmosphere, or a deoxidant having both a deoxidation function and a desiccation function.

Content of Compound A or salt thereof, or a hydrate thereof contained in the solid preparation used in the present invention is 1 to 99%.

The light, moisture, or oxygen nonpermeable container used in the present invention is not particularly limited so long as it can maintain a sealed state when the solid preparation is enclosed. Examples include, for example, glass bottle, aluminum can, aluminum bag, bag or bottle made from a metal foil laminate or metal-deposited plastics, and so forth.

Examples of the light, moisture, or oxygen hardly permeable container used in the present invention include plastic packaging containers such as polyethylene bottle and bag made from a resin film, and so forth.

Examples of packaging material that can be used to form plastic packaging containers include, for example, high density polyethylene, low density polyethylene, polypropylene, polyethylene terephthalate, polyvinyl idene chloride, polyvinyl chloride, polychlorotrifluoroethylene, polyvinyl alcohol, polyamide, polyethylene-cellophane laminate, ethylene-vinyl alcohol copolymer resin, polyacrylonitrile, and so forth, and a material consisting of a single kind of these or an appropriate laminate of these is used.

Hereafter, usefulness of the present invention will be explained with reference to preparation examples, examples, and comparative examples. However, the present invention is not limited by these examples.

Preparation Example 1

(1) Under a nitrogen atmosphere, 2-aminomalonamide (30 g, Tateyama Kasei) and oxalic acid (115 mg) were added to 2-propanol (600 mL), the mixture was heated to 82° C., and then triethyl orthoformate (106 mL, purity 99.5%, Nippoh Chemicals) was added dropwise to the mixture over 10 minutes. Then, the reaction mixture was stirred at 84° C. for 7 hours and 30 minutes. The reaction mixture was cooled to 57° C., and then water (30 mL) and concentrated hydrochloric acid (24 mL) were successively added to the reaction mixture. The reaction mixture was cooled to 5° C., and the crystals were collected by filtration, and washed with acetone (120 mL) to obtain 5-hydroxy-1H-imidazole-4-carboxamide hydrochloride dihydrate as pale yellow crystals (49 g).

(2) Under a nitrogen atmosphere, 5-hydroxy-1H-imidazole-4-carboxamide hydrochloride dihydrate (20.0 g) was added to 0.45 mol/L hydrochloric acid (240 mL), and dissolved therein by heating the mixture to 50° C. To this solution, a solution of sodium formate (14.3 g) dissolved in water (40 mL) was added dropwise over 33 minutes. The reaction mixture was cooled to 5° C., and the crystals were collected by filtration, washed with a mixture of acetone (20 mL) and water (40 mL), and then washed with acetone (60 mL) to obtain 5-hydroxy-1H-imidazole-4-carboxamide 3/4 hydrate as pale yellow crystals (12.8 g).

Example 1

(1) Preparation of White Solid Preparation

As a hydrate of Compound A, ¾ hydrate of Compound A produced by a method similar to the method described in Preparation Example 1 was used.

To the hydrate of Compound A (442.52 g) ground by using a pin mill grinder (ALPINE Microgrinder 630, Powrex), lactose hydrate (27.88 g, Pharmatose 200M, DMV-Fonterra Excipients) sieved through an 850 μm-mesh sieve, and carmellose calcium (44.82 g, ECG-505, Nichirin Chemical Industries) were added. On the obtained mixture, an aqueous dispersion containing light anhydrous silicic acid (16.80 g, Aerosil 200, Nippon Aerosil) dispersed in a solution of hydroxypropylcellulose (16.79 g, HPC-L, Nippon Soda) dissolved in purified water (302.50 g, Purified Water, Kozakai Pharmaceutical) was sprayed, and the mixture was granulated by using a fluidized bed granulator (FD-MP-01, Powrex), and dried. This dried powder was subjected to size selection by passing it through a 1.0 mm-mesh sieve to obtain granulated powder. To the obtained granulated powder, magnesium stearate (9.41 g, Magnesium Stearate, Merck) sieved through a 180-μm mesh sieve was added, and the mixture was kneaded in a V-shaped mixer (Mixer Type S-5, Tsutsui Scientific Instruments, 3 L-volume) at 30 rpm for 30 minutes to obtain mixed powder for tablet making. This mixed powder was made into tablets (tableting pressure =about 10 kN, 20 rpm) by using a rotary tableting machine (HT-P18A, HATA) with a double curved surface pestle (12R×3R mm) for a tablet diameter of 8.5 mm to obtain circular uncoated tablets having a weight of 280 mg per tablet. The uncoated tablets were coated with a coating agent (Opadry 03A48081; composition, 60% of hypromellose 2910, 20% of talc, and 20% of titanium oxide; Colorcon Japan) in an amount of 12 mg per tablet by using a coating machine (DRC-200, Powrex), and then subjected to a glazing treatment by adding carnauba wax (Polishing Wax 105, Freund Corporation) in an amount of 54.70 mg per 364.77 g of the uncoated tablets to obtain film-coated tablets (diameter, about 8.6 mm; thickness, about 4.3 to 4.7 mm; circular shape).

(2) Preparation of Packaged Product

Three of the film-coated tablets obtained in (1) mentioned above were put into a glass bottle having an internal volume of 50 mL together with silica gel (2 g, Silica Gel SB2gN, sachet-packed, Marutani Chemical Plant & Engineering), and the bottle was closed with a stopper, and cartoned into a paper box to obtain a packaged product.

Example 2

Three of the film-coated tablets obtained in Example 1, (1) were put into a glass bottle having an internal volume of 50 mL together with one sachet of silica gel (2 g, Silica Gel SB2gN, sachet-packed, Marutani Chemical Plant & Engineering) and one sachet of Ageless Z-20PKC (Mitsubishi Gas Chemical), and the bottle was closed with a stopper, and cartoned into a paper box to obtain a packaged product.

Example 3

Three of the film-coated tablets obtained in. Example 1, (1) were put into a glass bottle having an internal volume of 50 mL together with one sachet of PharmaKeep KH-20 (Mitsubishi Gas Chemical), and the bottle was closed with a stopper, and cartoned into a paper box to obtain a packaged product.

Example 4

Three of the film-coated tablets obtained in Example 1, (1) were put into a glass bottle having an internal volume of 50 mL together with one sachet of PharmaKeep KD-20 (Mitsubishi Gas Chemical), and the bottle was closed with a stopper, and cartoned into a paper box to obtain a packaged product.

Example 5

Three of the film-coated tablets obtained in Example 1, (1) were put into a glass bottle having an internal volume of 50 mL together with one sachet of silica gel (2 g, Silica Gel SB2gN, sachet-packed, Marutani Chemical Plant & Engineering) and one sachet of PharmaKeep KH-20 (Mitsubishi Gas Chemical), and the bottle was closed with a stopper, and cartoned into a paper box to obtain a packaged product.

Example 6

Three of the film-coated tablets obtained in Example 1, (1) were put into a glass bottle having an internal volume of 20 mL together with one sachet of zeolite (1 g, MS Sanpo 1 g (F-9), Shin-etsu Kasei Kogyo, sachet-packed), and the bottle was closed with a stopper, and cartoned into a paper box to obtain a packaged product.

Example 7

(1) Preparation of White Solid Preparation

A hydrate of Compound A was produced by a method similar to the method described in Preparation Example 1.

To the hydrate of Compound A (221.29 g) ground by using a pin mill grinder (ALPINE Microgrinder 630, Powrex), lactose hydrate (13.95 g, Pharmatose 200M, DMV-Fonterra Excipients) sieved through a 500 μm-mesh sieve, and carmellose calcium (22.40 g, ECG-505, Nichirin Chemical Industries) were added. An aqueous dispersion containing light anhydrous silicic acid (18.03 g, Aerosil 200, Nippon Acrosil) dispersed in a solution of hydroxypropylcellulose (18.00 g, HPC-L, Nippon Soda) dissolved in ion-exchanged water (324.32 g, G-20B, ORGANO) was weighed in a weight of 168.04 g, and sprayed on the mixture obtained above, and the mixture was granulated by using a fluidized bed granulator (FD-MP-01, Powrex), and dried. To the obtained granulated powder (186.91 g), magnesium stearate (3.83 g, Magnesium Stearate, Merck) sieved through a 180-μm mesh sieve was added, and the mixture was kneaded in a V-shaped mixer (Mixer Type S-5, Tsutsui Scientific Instruments, 3 L-volume) at 30 rpm for 30 minutes to obtain mixed powder for tablet making. This mixed powder was made into tablets (tableting pressure, about 10 kN; 20 rpm) by using a rotary tableting machine (HT-P18A, HATA) with a double curved surface pestle (12R×3R mm) for a tablet diameter of 8.5 mm to obtain circular uncoated tablets having a weight of 280 mg per tablet. The uncoated tablets were coated with a coating agent (Opadry 03A48081; composition, 60% of hypromellose 2910, 20% of talc, and 20% of titanium oxide; Colorcon Japan) in an amount of 12 mg per tablet by using a coating machine (DRC-200, Powrex), and then subjected to a glazing treatment by adding carnauba wax (Polishing Wax 105, Freund Corporation) in an amount of 26.86 mg per 171.66 g of the coated tablets to obtain film-coated tablets (diameter, about 8.6 mm; thickness, about 4.3 to 4.7 mm; circular shape).

(2) Preparation of Packaged Product

Three of the film-coated tablets obtained in (1) mentioned above were PTP-packaged (heat sealing temperature, 150° C.; heat sealing pressure, 45 Hz; heat sealing time, 1.8 second) by using a semiautomatic PTP packaging machine (K200 LS, Daiwa Chemical Industry) with a molded polyvinyl chloride sheet (product number, R-1T; thickness, 225 to 275 μm; size, 196±2 mm×228±2 mm; arrangement of molded pockets, 10×8; Daiwa Chemical Industry) and an aluminum foil (material, aluminum; thickness, 18 to 22 μm; size, 205±2 mm×176±2 mm, Daiwa Chemical Industry). One sheet of this PTP-packaged product (10 tablets were contained in one sheet) and one sachet of PharmaKeep KD-20 (Mitsubishi Gas Chemical) were put into an aluminum bag (material, aluminum, polyethylene terephthalate and polyethylene; thickness, 67 to 81 μm; size, 85±2 mm×250±2 mm; Daiwa Chemical Industry), and the opening of the aluminum bag was closed by heat sealing (temperature, 150° C.; heating time, 2 seconds) by using a heat sealer (OPL-600-10, Fuji Impulse) to obtain a packaged product.

Example 8

(1) Preparation of Subtilized Granules

A hydrate of Compound A was produced by a method similar to the method described in. Preparation Example 1.

The hydrate of Compound A (10.608 g) sieved through a 500-μm mesh sieve, and cornstarch (0.638 g, Cornstarch, Nihon Shokuhin Kako) were put into a mortar, and mixed. A solution of cornstarch (2.0 g) and anhydrous citric acid (Anhydrous citric acid, Komatsuya Corporation) dissolved in ion-exchanged water (17.929 g, G-20B, ORGANO) was weighed in a weight of 1.344 g, and ion-exchanged water (5.376 g) was added to the solution to prepare a binder solution. The mixture containing the hydrate of Compound A was granulated with adding the binder solution (6.72 g) to the mortar. The obtained granulated powder was dried at 40° C. for 2 hours, and passed through a 500-μm mesh sieve to obtain subtilized granules.

(2) Preparation of Packaged Product

The subtilized granules obtained (1) mentioned above were divided and packed in sachets for subtilized granules (material, cellophane and polyethylene) in an amount of 1 g per sachet using a heat sealer (OPL-600-10, Fuji Impulse) to obtain sachet-packed subtilized granules. One sachet of the sachet-packed subtilized granules and one sachet of PharmaKeep KD-20 (Mitsubishi Gas Chemical) were put into an aluminum bag (material, aluminum, polyethylene terephthalate and polyethylene; thickness, 67 to 81 μm; size, 85±2 mm×250±2 mm; Daiwa Chemical Industry), and the opening of the aluminum bag was closed by heat sealing (temperature, 150° C.; heating time, 2 seconds) by using a heat sealer (OPL-600-10, Fuji Impulse) to obtain a packaged product.

Comparative Example 1

Three of the film-coated tablets obtained in Example 1, (1) were put into a glass bottle having an internal volume of 50 mL, and the bottle was closed with a stopper, and cartoned into a paper box to obtain a packaged product.

Comparative Example 2

Three of the film-coated tablets obtained in Example 1, (1) were put into a glass bottle having an internal volume of 50 mL together with one sachet of Ageless Z-20PKC (Mitsubishi Gas Chemical), and the bottle was closed with a stopper, and cartoned into a paper box to obtain a packaged product.

Comparative Example 3

One sachet of the sachet-packed subtilized granules obtained in Example 8, (2) was put into an aluminum bag (material, aluminum, polyethylene terephthalate and polyethylene; thickness, 67 to 81 μm; size, 85±2 mm×250±2 min; Daiwa Chemical Industry), the opening of the aluminum bag was closed by heat sealing (temperature, 150° C.; heating time, 2 seconds) by using a heat sealer (OPL-600-10, Fuji Impulse), and the aluminum bag was cartoned into a paper box to obtain a packaged product.

Test Example 1

The packaged products of Examples 1 to 5 and Comparative Examples 1 and 2 were stored at 60° C. for four weeks.

At the time of the start of the test, and after the storage, $L^*$ (lightness) as well as $a^*$ and $b^*$ (hue, saturation) of the tablet surfaces of the film coated tablets were measured by using a spectral color difference meter (SE2000; C-light source; viewing angle, 2°; pore diameter for tablet, 6 mm; Nippon Denshoku Industries), and color differences ($\Delta E^*$) were calculated. The color differences ($\Delta E^*$) were calculated from the differences of $L^*$, $a^*$, and $b^*$ of the samples measured before and after the test in accordance with the following equation.

$$\Delta E^* = \{(\Delta L^*)^2 + (\Delta a^*)^2 + (\Delta b^*)^2\}^{1/2}$$

The results are shown in Table 1.

TABLE 1

|  | Deoxidant | Desiccant | Color difference ($\Delta E$) |
| --- | --- | --- | --- |
| Example 1 | None | Silica gel | 1.22 |
| Example 2 | Ageless Z-20PKC | Silica gel | 1.12 |
| Example 3 | PharmaKeep KH-20 | None | 2.01 |
| Example 4 | PharmaKeep KD-20 |  | 0.96 |
| Example 5 | PharmaKeep KH-20 | Silica gel | 0.94 |
| Comparative Example 1 | None | None | 3.48 |
| Comparative Example 2 | Ageless Z-20PKC | None | 7.68 |

When any desiccant and deoxidant were not used (Comparative Example 1), the color difference ($\Delta E^*$) was 3.48, and thus discoloration of the tablet was observed. Further, when only the self-activating type deoxidant was coexisted (Comparative Example 2), the color difference ($\Delta E^*$) was 7.68, and thus marked discoloration was observed.

On the other hand, when the desiccant (silica gel) was coexisted (Example 1), and when the desiccant (silica gel) and the self-activating type deoxidant (Ageless Z-20PKC) were coexisted (Example 2), the color differences ($\Delta E^*$) were 1.22 and 1.12, respectively, thus discoloration was not observed, and discoloration-preventing effect was exhibited.

Further, when a carbon-carbon unsaturated bond oxidation type deoxidant (PharmaKeep KH-20) was coexisted (Example 3), the color difference ($\Delta E^*$) was 2.01, thus discoloration was not observed in such a degree that it can be recognized with naked eyes, and discoloration-suppressing effect was exhibited without using any desiccant.

Furthermore, when the deoxidant (PharmaKeep KD-20) comprising a deoxidant using oxidation of carbon-carbon unsaturated bond and silica gel combined beforehand was coexisted (Example 4), and when the desiccant (silica gel) and the carbon-carbon unsaturated bond oxidation type deoxidant (PharmaKeep KH-20) were coexisted (Example 5), the color differences ($\Delta E^*$) were 0.96 and 0.94, respectively, and thus marked discoloration-preventing effect was exhibited.

Test Example 2

The packaged product of Example 6 was stored at 60° C. for four weeks. The color difference ($\Delta E^*$) of the tablet surface of the film-coated tablet was obtained in the same manner as that of Test Example 1.

As a result, the color difference ($\Delta E^*$) was 1.96.

Discoloration was not observed in the tablets after the storage, and discoloration-preventing effect was exhibited.

Test Example 3

The packaged product of Example 7 was stored under the conditions of 40° C. and a relative humidity of 75% for three months.

The color difference ($\Delta E^*$) of the tablet surface of the film-coated tablet was obtained in the same manner as that of Test Example 1.

As a result, the color difference ($\Delta E^*$) was 1.17.

Discoloration was not observed in the tablets after the storage.

Test Example 4

The packaged products of Example 8 and Comparative Example 3 were stored at 60° C. for four weeks.

The color differences ($\Delta E^*$) of the subtilized granules were obtained in the same manner as that of Test Example 1.

As a result, the color difference ($\Delta E^*$) was 6.75 for the product of Comparative Example 3, and thus marked discoloration of the subtilized granules was observed. On the other hand, when the deoxidant (PharmaKeep KD-20) comprising a deoxidant using oxidation of carbon-carbon unsaturated bond and silica gel combined beforehand was coexisted (Example 8), the color difference ($\Delta E^*$) was 2.51, and thus marked discoloration-preventing effect was exhibited.

INDUSTRIAL APPLICABILITY

The present invention provides a packaged product of a solid preparation containing Compound A or a salt thereof, or a hydrate thereof that shows sufficient storage stability required for practical use of the solid preparation, by packaging the solid preparation together with an environment-controlling agent.

The packaged product of present invention is useful as a storage form of a solid preparation containing Compound A or a salt thereof with which discoloration of the solid preparation is suppressed, and superior storage stability of the solid preparation is obtained.

The invention claimed is:

1. A packaged product of a solid preparation containing 5-hydroxy-1H-imidazole-4-carboxamide or a salt thereof, or a hydrate thereof, which comprises the solid preparation and an environment-controlling agent packaged together, wherein the environment-controlling agent is (A) a desiccant or (B) a deoxidant having both a deoxidation function and a desiccation function.

2. The packaged product of the solid preparation according to claim 1, wherein the environment-controlling agent is a desiccant.

3. The packaged product according to claim 2, wherein the desiccant is silica gel.

4. The packaged product of the solid preparation according to claim 2, wherein the packaged product further contains a deoxidant that exhibits a deoxidation function in a dry atmosphere.

5. The packaged product of the solid preparation according to claim 4, wherein the deoxidant that exhibits a deoxidation function in a dry atmosphere is a deoxidant using oxidation of carbon-carbon unsaturated bond.

6. The packaged product of the solid preparation according to claim 2, wherein the packaged product further contains a self-activating type deoxidant.

7. The packaged product of the solid preparation according to claim 3, wherein the packaged product further contains a self-activating type deoxidant.

8. A method for stabilizing a solid preparation containing 5-hydroxy-1H-imidazole-4-carboxamide or a salt thereof, or a hydrate thereof, which comprises packaging the solid preparation together with an environment-controlling agent, wherein the environment-controlling agent is (A) a desiccant or (B) a deoxidant having both a deoxidation function and a desiccation function.

9. The method for stabilizing a solid preparation according to claim 8, wherein the environment-controlling agent is a desiccant.

10. The method for stabilizing a solid preparation according to claim 8, wherein the desiccant is silica gel.

11. The method for stabilizing a solid preparation according to claim 9, wherein a deoxidant that exhibits a deoxidation function in a dry atmosphere is further packaged together.

12. The method for stabilizing the solid preparation according to claim 11, wherein the deoxidant that exhibits a deoxidation function in a dry atmosphere is a deoxidant using oxidation of carbon-carbon unsaturated bond.

13. The method for stabilizing the solid preparation according to claim 9, wherein a self-activating type deoxidant is further packaged together.

\* \* \* \* \*